(12) United States Patent
Cash

(10) Patent No.: US 11,865,092 B2
(45) Date of Patent: Jan. 9, 2024

(54) METHOD TO ALLEVIATE THE SYMPTOMS OF PMS

(71) Applicant: Alan B. Cash, San Diego, CA (US)

(72) Inventor: Alan B. Cash, San Diego, CA (US)

(*) Notice: Subject to any disclaimer, the term of this patent is extended or adjusted under 35 U.S.C. 154(b) by 201 days.

(21) Appl. No.: 17/354,866

(22) Filed: Jun. 22, 2021

(65) Prior Publication Data

US 2021/0308083 A1   Oct. 7, 2021

Related U.S. Application Data

(62) Division of application No. 16/335,652, filed as application No. PCT/US2017/052718 on Sep. 21, 2017, now Pat. No. 11,071,722.

(60) Provisional application No. 62/398,319, filed on Sep. 22, 2016.

(51) Int. Cl.
| | | |
|---|---|---|
| *A61K 31/194* | (2006.01) | |
| *A61K 31/167* | (2006.01) | |
| *A61K 31/192* | (2006.01) | |
| *A61K 31/4402* | (2006.01) | |
| *A61K 31/522* | (2006.01) | |

(52) U.S. Cl.
CPC .......... *A61K 31/194* (2013.01); *A61K 31/167* (2013.01); *A61K 31/192* (2013.01); *A61K 31/4402* (2013.01); *A61K 31/522* (2013.01)

(58) Field of Classification Search
CPC .................................................. A61K 31/194
See application file for complete search history.

(56) References Cited

U.S. PATENT DOCUMENTS

| | | |
|---|---|---|
| 2,798,053 A | 7/1957 | Brown |
| 4,573,996 A | 3/1986 | Kwiatek |
| 4,597,961 A | 7/1986 | Etscorn |
| 4,670,248 A | 6/1987 | Schricker |
| 4,839,174 A | 6/1989 | Baker |
| 4,908,213 A | 3/1990 | Govil |
| 4,943,435 A | 7/1990 | Baker |
| 5,155,105 A | 10/1992 | Jones |
| 5,328,454 A | 7/1994 | Sibalis |
| 5,336,168 A | 8/1994 | Sibalis |
| 5,474,527 A | 12/1995 | Bettinger |
| 5,498,631 A | 3/1996 | Gorbach |
| 5,569,459 A | 10/1996 | Shlyankevich |
| 5,612,061 A | 3/1997 | Rabkin |
| 5,654,011 A | 8/1997 | Jackson |
| 5,676,969 A | 10/1997 | Wick |
| 5,707,630 A | 1/1998 | Morrow |
| 5,760,630 A | 6/1998 | Okamoto |
| 6,057,439 A | 5/2000 | Jennings-white |
| 6,174,542 B1 | 1/2001 | Hinton |
| 6,322,823 B1 | 11/2001 | Mannella |
| 6,987,101 B1 | 1/2006 | Nashed |
| 7,473,426 B2 | 1/2009 | Choe |
| 7,858,605 B2 | 12/2010 | Bell |
| 7,897,147 B2 | 3/2011 | Dadas |
| 8,124,598 B2 | 2/2012 | Sageman |
| 8,338,396 B2 | 12/2012 | Bell |
| 8,399,432 B2 | 3/2013 | Rutenberg |
| 8,680,084 B2 | 3/2014 | Bell |
| 8,772,301 B2 | 7/2014 | Hardy |
| 9,050,306 B2 | 6/2015 | Cash |
| 9,561,199 B2 | 2/2017 | Cash |
| 11,071,722 B2* | 7/2021 | Cash ...................... A61K 45/06 |
| 2003/0119913 A1 | 6/2003 | Ohia |
| 2006/0217303 A1 | 9/2006 | Kriegler |
| 2008/0279786 A1 | 11/2008 | Cash |
| 2013/0143930 A1 | 6/2013 | Cash |
| 2019/0321315 A1 | 10/2019 | Cash |

FOREIGN PATENT DOCUMENTS

| | | |
|---|---|---|
| AU | 2005316295 B2 | 6/2006 |
| CA | 2589995 C | 1/2016 |
| EP | 1824470 A2 | 8/2007 |
| EP | 3056199 A1 | 8/2016 |
| JP | 5268362 B2 | 5/2013 |
| WO | 199738701 A1 | 10/1997 |
| WO | 199921565 A1 | 5/1999 |
| WO | 2006066244 A2 | 6/2006 |
| WO | 2006066244 A3 | 2/2007 |
| WO | 2015112671 A1 | 7/2015 |

OTHER PUBLICATIONS

Carvalho, A.S. et al. (Feb. 2011, e-pub. Dec. 24, 2010). "Neuroprotective Effect Of Pyruvate and Oxaloacetate During Pilocarpine Induced Status Epilepticus In Rats," Neurochemistry International 58(3):385-390.
Cash, A. (Apr. 12, 2013). "Oxaloacetate Supplementation: Modification of the NAD+/NADH Ratio to Mimic Calorie Restriction," Terra Biological LLC , 43 pages.
Cash, A. (Mar. 26, 2014). "Oxaloacetate Supplementation: Modification of the NAD+/NADH Ration To Mimic Calorie Restriction," Terra Biological LLC, 52 pages.
Gao, X. et al. (Dec. 2014, e-pub. Sep. 26, 2014). "Shu-Yu Capsule, A Traditional Chinese Medicine Formulation, Attenuates Premenstrual Syndrome Depression Induced By Chronic Stress Constraint," Molecular Medicine Reports 10(6):2942-2948.
International Preliminary Report on Patentability dated Apr. 4, 2019 for PCT Application No. PCT/US2017/052718, filed on Sep. 21, 2017, 6 pages.
International Search Report and Written Opinion dated Dec. 1, 2017 for PCT Application No. PCT/US2017/052718, filed on Sep. 21, 2017, 8 pages.

(Continued)

*Primary Examiner* — Rei Tsang Shiao
(74) *Attorney, Agent, or Firm* — MORRISON & FOERSTER LLP

(57) ABSTRACT

The invention relates to methods for treating symptoms of PMS and PMDD including muscle ache, bloating, cramping, acne, tender breasts, bloating, fatigue, difficulty concentrating, diminished impulse control, irritability, anxiety, tension, anger, depression, insomnia and/or rapid fluctuations in mood (mood swings). The method comprises administration of a pharmaceutical composition comprising oxaloacetate, oxaloacetate salts, oxaloacetic acid and/or anhydrous enol-oxaloacetate.

23 Claims, 1 Drawing Sheet

(56) References Cited

OTHER PUBLICATIONS

Liang, B. MD. (Aug. 2003). "Recognizing and Treating Premenstrual Dysphoric Disorder," Hospital Physician pp. 45-57.

Ruban, A et al. (Feb. 2014, e-pub. Oct. 23, 2013). "Blood Glutamate Scavenging As A Novel Neuroprotective Treatment For Paraoxon Intoxication," Journal of Cerebral Blood Flow & Metabolism 34(2):221-227.

Sabat, R. et al. (2012, e-pub. Feb. 16, 2012). "Increased Prevalence of Metabolic Syndrome In Patients With Acne Inversa," PLoS One 7(2):e31810, 9 pages.

Yamamoto, H.A. et al. (Jul. 20, 2003). "Effect of Alpha-Ketoglutarate and Oxaloacetate On Brain Mitochondrial DNA Damage and Seizures Induced By Kainic Acid In Mice," Toxicology Letters 143(2):115-122.

Yoshikawa, K. (Oct. 1968). "Studies on Anti-Diabetic Effect of Sodium Oxaloacetate," Tohoku J. exp. Med. 96(2):127-141.

Zlotnik, A et al. (Jul. 2009). "The Neuroprotective Effects of Oxaloacetate in Closed Head Injury in Rats is Mediated by its Blood Glutamate Scavenging Activity: Evidence From the Use of Maleate," J Neurosurg. Anesthesiol. 21(3):235-241.

\* cited by examiner

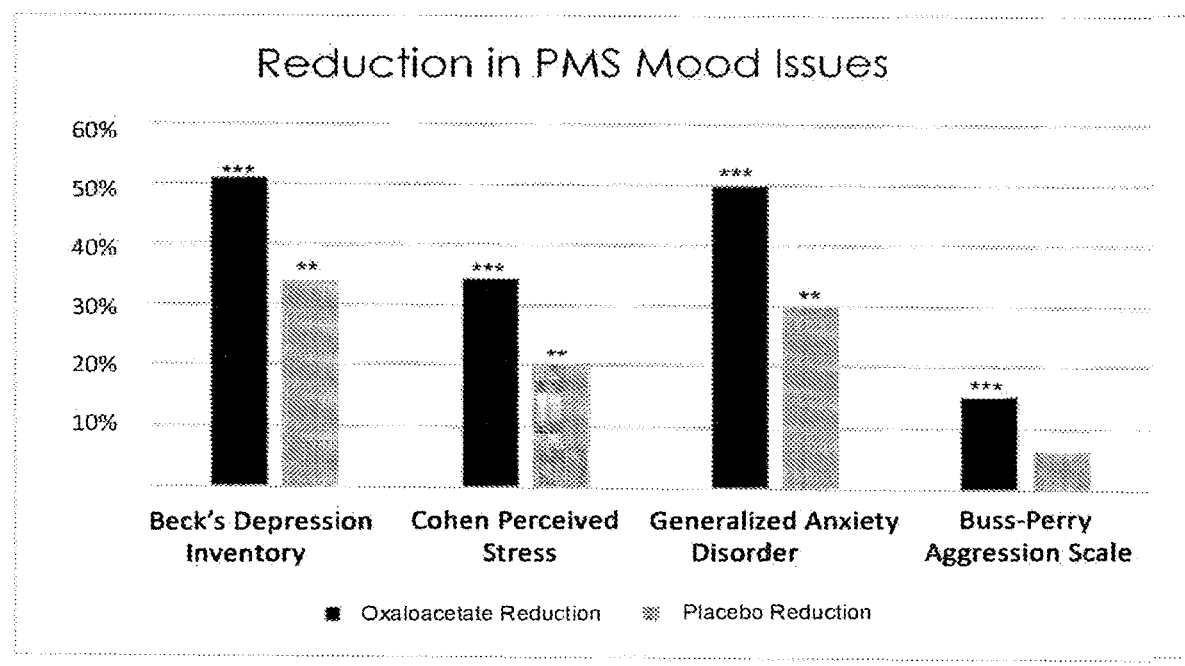

METHOD TO ALLEVIATE THE SYMPTOMS OF PMS

CROSS REFERENCE TO RELATED APPLICATIONS

This application is a divisional application of U.S. patent application Ser. No. 16/335,652, which adopts the international filing date of Sep. 21, 2017, which is a national stage application under 35 U.S.C. § 371 of International Application No. PCT/US2017/052718, filed internationally on Sep. 21, 2017, which claims the benefit of U.S. Provisional Application No. 62/398,319, filed Sep. 22, 2016, the contents of which are hereby incorporated by reference in their entirety.

TECHNICAL FIELD

The present application relates generally to methods for treating symptoms of premenstrual syndrome (PMS), including Premenstrual Dysphoric Disorder (PMDD), comprising administering a composition comprising oxaloacetate to a subject in need thereof.

BACKGROUND

Premenstrual Syndrome (PMS) is a group of physical and mental symptoms which occur cyclically beginning about seven to fourteen days prior to menses in the luteal phase of the menstrual cycle. Menstruation occurs in women from the age of about twelve to thirteen (on average) until approximately 50 years old. The menstrual cycle averages about twenty-eight days with some variation. Common PMS symptoms include muscle ache, bloating, cramping, acne, tender breasts, bloating, fatigue, difficulty concentrating, diminished impulse control, irritability, anxiety, tension, anger, depression, feeling "out of control", insomnia and rapid fluctuations in mood (mood swings) Suicidal thoughts are also sometimes reported. The symptoms typically resolve with the start of menstruation. While there are commercially available treatments for physical discomforts, acne, and bloating, there are fewer options available for fatigue, difficulty concentrating, diminished impulse control, irritability, anxiety, tension, anger, depression, feeling "out of control", suicidal thoughts, insomnia and rapid fluctuations in mood (mood swings).

Premenstrual Dysphoric Disorder (PMDD) is a severe form of PMS that affects 3-8% of menstruating women. Additional information on both PMS and PMDD can be found in the Diagnostic and Statistical Manual of Mental Disorders, Fifth Edition, edited by the American Psychiatric Association. Treatment of the many of the symptoms of PMDD is largely with antidepressants that modulate serotonin levels in the brain via serotonin reuptake inhibitors (SRIs). These lead to an increase in extracellular concentrations of serotonin. These SRIs can have devastating side effects, including sexual dysfunction and suicidal behavior. Additional SRI side effects can include insomnia, skin rashes, headaches, joint and muscle pain, stomach upset, nausea, and diarrhea, thereby making some of the PMDD symptoms worse.

There have been some treatments for PMS and PMDD: U.S. Pat. No. 8,680,084 provides for a method of treating PMS and PMDD with oral contraceptives. U.S. Pat. Nos. 8,338,396 and 7,858,605 also provide for this method.

U.S. Pat. No. 8,399,432 uses a pharmaceutical/nutritional composition for PMS and PMDD using phospholipase-D.

U.S. Pat. No. 8,124,598 discloses the use of 7-keto DHEA for treating PMS.

U.S. Pat. No. 7,897,147 uses botulinum toxin to treat symptoms of premenstrual disorder.

U.S. Pat. No. 6,987,101 uses gestagen (drospirenone) for treating PMDD.

U.S. Pat. Nos. 6,322,823/6,174,542, 5,612,061, 5,569,459, 5,498,631, 5,654,011, 5,707,630 and 5,760,630 all contain mixtures of vitamins, minerals, essential oils and dietary supplements for the treatment of PMS.

U.S. Pat. No. 6,057,439 provides for the use of steroids to treat PMS.

U.S. Pat. No. 7,4373,426 uses yeast extract as a method to inhibit reuptake of serotonin and norepinephrine for the treatment of PMS.

U.S. Pat. No. 8,772,301 (Hardy, et al.) provides for compounds that modulate the activity of metabotropic glutamate receptor 5 (mGluR5) in the central nervous system or the periphery for the treatment of PMS and PMDD.

Gao, et al, "Shu-Yu capsule, a Traditional Chinese Medicine formulation, attenuates premenstrual syndrome depression induced by chronic stress constraint" Molecular Medicine Reports, 10:2942-2948 (2014) show efficacy with a herbal formulation to reduce the depression of glutamate in a rat model of PMS, indicating that low glutamate levels may be the problem in PMS.

Oxaloacetate is a small molecule human metabolite with high bioavailability involved in many reactions in the body, including the citric cycle within the mitochondria, gluconeogenesis, urea cycle, glyoxylate cycle, amino acid synthesis, and fatty acid synthesis.

Oxaloacetate has been examined for the following conditions:
- As a mimic of calorie restriction (Cash, U.S. Pat. No. 2,005,316295 Australia)
- To Increase human lifespan (Cash, U.S. Pat. No. 5,268,362 Japan)
- For Cancer (Cash, EPO 05 854 787.8-1464, Canada 2,589,995)
- For Parkinson's and Alzheimer Disease (Cash, USPTO 20080279786)
- To Activate AMPK (Cash, USPTO 20130143930)
- For diabetes (Yoshikawa, "Studies on Anti-diabetic Effect of Sodium Oxaloacetate" Tohoku J. exp. Med, 1968, 96, 127-141)
- For closed head injury (Zlotnik, A et al, "The Neuroprotective Effects of Oxaloacetate in Closed Head Injury in Rats is Mediated by its Blood Glutamate Scavenging Activity", J Neurosurg Anesthesiol 21, 3 Jul. 2009
- For protection against pesticides (Ruban, A et al, "Blood glutamate scavenging as a novel neuroprotective treatment for paraoxon intoxication" Journal of Cerebral Blood Flow & Metabolism (2014) 34, 221-227)
- For epileptic seizures Carvalho, et al, "Neuroprotective effect of pyruvate and oxaloacetate during pilocarpine induced status epilepticus in rats" Neurochemistry International 58 (2011 385-390 also Kriegler, S US Patent application 20060217303)
- For protection against some poisons, such as Kainic acid (Yamamoto, et al, "Effect of alpha-ketoglutarate and oxaloacetate on brain mitochondrial DNA damage and seizures induced by Kainic acid in mice" Toxicology Letters 143 (2003) 115-122

All references cited herein, including patent applications and publications, are incorporated by reference in their entirety.

SUMMARY OF THE INVENTION

In some aspects, the present invention is directed to methods for treating the symptoms of Premenstrual Syndrome (PMS) with a therapeutic containing one or more oxaloacetate compounds from the group of an oxaloacetate, an oxaloacetate salt, and/or an oxaloacetic acid (hereinafter, "oxaloacetate" in this specification). In some aspects, the present invention is directed to methods for treating the symptoms of Premenstrual Dysphoric Disorder (PMDD) with a therapeutic containing one or more oxaloacetate compounds from the group of an oxaloacetate, an oxaloacetate salt, and/or an oxaloacetic acid (hereinafter, "oxaloacetate" in this specification). These symptoms include mood swings, anger, anxiety, depression and fatigue.

In some embodiments of the invention, the oxaloacetic acid for use in methods to treat PMS will be in a stable form such as anhydrous enol-oxaloacetic acid. In some embodiments of the invention, the oxaloacetic acid for use in methods to treat PMDD will be in a stable form such as anhydrous enol-oxaloacetic acid.

In some embodiments of the invention, the oxaloacetate compound further comprises an acceptable pharmaceutical carrier. This carrier can be encapsulation agents such as hypromellose capsules or other low water-content capsules. Alternatively, the oxaloacetate can be compressed into a tablet with such carriers as calcium carbonate, dicalcium phosphate, erythitol, vegetable steric acid, and ascorbyl palmitate. Further, said oxaloacetate, can be delivered via a two-phase system, in which water or other water based fluids are held separately from said oxaloacetate, and only combined just prior to ingestion. Still further, said oxaloacetate can be placed in a low-water content transdermal patch and delivered trans-dermally. Yet still further, said oxaloacetate can be mixed with water and a pH buffer and then immediately delivered through an inhalation system. Said oxaloacetate can also be delivered to the body via suppository or when mixed with water based fluids and a pH modifier, via injection or intravenous infusion.

In another embodiment of the invention, said oxaloacetate can be combined with a pain reliever and/or an anti-bloating agent for the symptoms of cramping and bloating associated with PMS, respectively. In another embodiment of the invention, said oxaloacetate can be combined with a pain reliever and/or an anti-bloating agent for the symptoms of cramping and bloating associated with PMDD, respectively.

In some embodiments, the oxaloacctate compound comprises a water barrier to shield the compound from absorbing atmospheric moisture to assure proper shelf life and prevent degradation into carbon dioxide and pyruvate.

In some aspects, the invention provides a method for treating one or more symptoms of premenstrual syndrome (PMS) in an individual, the method comprising administering an effective amount of a composition comprising an oxaloacetate, an oxaloacetic acid, or an oxaloacetate salt to an individual in need thereof; wherein the one or more symptoms of PMS include one or more of acne, tender breasts, bloating, fatigue, difficulty concentrating, diminished impulse control, irritability, anxiety, tension, anger, depression, suicidal thoughts, insomnia, or cramping. In some embodiments, the method is for treating two or more symptoms of PMS in an individual, wherein the two or more symptoms of PMS include two or more of acne, tender breasts, bloating, fatigue, difficulty concentrating, diminished impulse control, irritability, anxiety, tension, anger, depression, suicidal thoughts, insomnia, or cramping. In some embodiments, the method is for treating three or more symptoms of PMS in an individual, wherein the three or more symptoms of PMS include three or more of acne, tender breasts, bloating, fatigue, difficulty concentrating, diminished impulse control, irritability, anxiety, tension, anger, depression, suicidal thoughts, insomnia, or cramping. In some embodiments, the symptoms of PMS include acne, bloating, fatigue, irritability, anxiety, anger, depression, insomnia or cramping. In some embodiments, the one or more symptoms of PMS further comprises mood swings.

In some embodiments of the above aspects and embodiments, the oxaloacetate or oxaloacetic acid is anhydrous enol-oxaloacetate. In some embodiments, the composition further comprises a pharmaceutical delivery agent. In some embodiments, the pharmaceutical delivery agent is selected amongst the group of capsules, coating agents, encapsulating agents, transdermal patches, dissolving lozenges, suppositories and biphasic delivery systems. In some embodiments, the pharmaceutical delivery agent prevents or reduces exposure of the oxaloacetate to water. In some embodiments, the composition further comprises a pH modifier. In some embodiments, wherein the pH modifier is sodium hydroxide or calcium carbonate.

In some aspects, the invention provides a method for treating Premenstrual Dysphoric Disorder (PMDD) in an individual, the method comprising administering an effective amount of a composition comprising an oxaloacetate, an oxaloacetic acid, or an oxaloacetate salt in the individual in need thereof. In some embodiments, the invention provides a method for treating one or more symptoms of PMDD in an individual, the method comprising administering an effective amount of a composition comprising an oxaloacetate, an oxaloacetic acid, or an oxaloacetate salt to an individual in need thereof; wherein the one or more symptoms of PMS include one or more of acne, tender breasts, bloating, fatigue, difficulty concentrating, diminished impulse control, irritability, anxiety, tension, anger, depression, suicidal thoughts, insomnia, or cramping. In some embodiments, the method is for treating two or more symptoms of PMS in an individual, wherein the two or more symptoms of PMS include two or more of acne, tender breasts, bloating, fatigue, difficulty concentrating, diminished impulse control, irritability, anxiety, tension, anger, depression, suicidal thoughts, insomnia, or cramping. In some embodiments, the method is for treating three or more symptoms of PMS in an individual, wherein the three or more symptoms of PMS include three or more of acne, tender breasts, bloating, fatigue, difficulty concentrating, diminished impulse control, irritability, anxiety, tension, anger, depression, suicidal thoughts, insomnia, or cramping. In some embodiments, the symptoms of PMS include acne, bloating, fatigue, irritability, anxiety, anger, depression, insomnia or cramping. In some embodiments, the one or more symptoms of PMS further comprises mood swings.

In some embodiments of the above aspects and embodiments, the oxaloacetate or oxaloacetic acid is anhydrous enol-oxaloacetate. In some embodiments, the composition further comprises a pharmaceutical delivery agent. In some embodiments, the pharmaceutical delivery agent is selected amongst the group of capsules, coating agents, encapsulating agents, transdermal patches, dissolving lozenges, suppositories and biphasic delivery systems. In some embodiments, the pharmaceutical delivery agent prevents or reduces exposure of the oxaloacetate to water. In some embodiments, the composition further comprises a pH modifier. In some embodiments, wherein the pH modifier is sodium hydroxide or calcium carbonate.

In some embodiments of the above aspects and embodiments, the composition comprises about 100 or about 200, about 300 or about 400 mg oxaloacetate (e.g., anhydrous oxaloacetate). In some embodiments, about 200 mg oxaloacetate is administered to the individual per day. In some embodiments, the composition is administered over a period of about one day, two days, three days, four days or five days. In some embodiments, the composition is administered to the individual about one day, two days, three days, four days or five days prior to menses. In some embodiments, administration of the composition is initiated upon detection of one or more symptoms of PMS.

In some embodiments, the composition is administered in combination with a pain reliever. In some embodiments, the pain reliever is acetaminophen, ibuprofen, or naproxen. In some embodiments, about 500 mg acetaminophen is administered to the individual. In some embodiments, about 400 mg ibuprofen is administered to the individual. In some embodiments, about 220 mg naproxen sodium is administered to the individual. In some embodiments, the composition is administered in combination with an anti-bloating agent. In some embodiments, the anti-bloating agent is pyrilamine maleate or pamabrom. In some embodiments, about 15 mg pyrilamine maleate is administered to the individual. In some embodiments, about 25 mg pamabrom is administered to the individual. In some embodiments, the composition is administered with a pain reliever and with an anti-bloating agent.

In some aspects, the invention provides a composition comprising an oxaloacetate, an oxaloacetic acid, or an oxaloacetate salt and an anti-bloating agent. In some embodiments, the anti-bloating agent is pyrilamine maleate or pamabrom. In some embodiments, the composition comprises about 15 mg pyrilamine maleate. In some embodiments, the composition comprises about 25 mg pamabrom. In some aspects, the invention provides a composition comprising an oxaloacetate, an oxaloacetic acid, or an oxaloacetate salt and a pain reliever. In some embodiments, the pain reliever is acetaminophen, ibuprofen, or naproxen. In some embodiments, the composition comprises about 500 mg acetaminophen. In some embodiments, the composition comprises about 400 mg ibuprofen. In some embodiments, the composition comprises about 220 mg naproxen sodium. In some embodiments, the composition comprises oxaloacetate, a pain reliever and an anti-bloating agent. In some embodiments, the oxaloacetate or oxaloacetic acid is anhydrous enol-oxaloacetate. In some embodiments, the composition further comprises a pharmaceutical delivery agent. In some embodiments, the pharmaceutical delivery agent is selected amongst the group of capsules, coating agents, encapsulating agents, transdermal patches, dissolving lozenges, suppositories and biphasic delivery systems. In some embodiments, the pharmaceutical delivery agent prevents or reduces exposure of the oxaloacetate to water. In some embodiments, the composition further comprises a pH modifier. In some embodiments, wherein the pH modifier is sodium hydroxide or calcium carbonate. In some embodiments, the composition comprises about 10 mg oxaloacetate to about 1000 mg oxaloacetate. In some embodiments, the composition comprises about 100 mg or about 200 mg oxaloacetate.

In some aspects, the invention provides a method for treating one or more symptoms of premenstrual syndrome (PMS) in an individual, the method comprising administering an effective amount of a composition comprising an oxaloacetate, an oxaloacetic acid, or an oxaloacetate salt to an individual in need thereof; wherein the one or more symptoms of PMS include one or more of anger, anxiety, depression, or irritability. In some embodiments, the method is for treating two or more symptoms of premenstrual syndrome (PMS) in an individual, wherein the two or more symptoms of PMS include one or more of anger, anxiety, depression, or irritability. In some embodiments, the method is for treating three or more symptoms of premenstrual syndrome (PMS) in an individual, wherein the three or more symptoms of PMS include three or more of anger, anxiety, depression, or irritability. In some embodiments, the method is for treating anger, anxiety, depression, or irritability. In some embodiments, the one or more symptoms of PMS further comprises mood swings. In some embodiments, the PMS is PMDD. In some embodiments, the oxaloacetate or oxaloacetic acid is anhydrous enol-oxaloacetate. In some embodiments, the composition further comprises a pharmaceutical delivery agent. In some embodiments, the pharmaceutical delivery agent is selected amongst the group of capsules, coating agents, encapsulating agents, transdermal patches, dissolving lozenges, suppositories and biphasic delivery systems. In some embodiments, the pharmaceutical delivery agent prevents or reduces exposure of the oxaloacetate to water. In some embodiments, the composition further comprises a pH modifier. In some embodiments, wherein the pH modifier is sodium hydroxide or calcium carbonate. In some embodiments, the composition comprising the oxaloacetate is administered in combination with a pain reliever. In some embodiments, the pain reliever is acetaminophen, ibuprofen, or naproxen. In some embodiments, about 500 mg acetaminophen is administered to the individual. In some embodiments, about 400 mg ibuprofen is administered to the individual. In some embodiments, about 220 mg naproxen sodium is administered to the individual. In some embodiments, the composition comprising the oxaloacetate is administered in combination with an anti-bloating agent. In some embodiments, the anti-bloating agent is pyrilamine maleate or pamabrom. In some embodiments, about 15 mg pyrilamine maleate is administered to the individual. In some embodiments, about 25 mg pamabrom is administered to the individual. In some embodiments, the composition is administered with a pain reliever and with an anti-bloating agent.

In some aspects, the invention provides a method for treating one or more symptoms of premenstrual syndrome (PMS) in an individual, the method comprising administering an effective amount of a composition comprising an oxaloacetate, an oxaloacetic acid, or an oxaloacetate salt to an individual in need thereof; wherein the one or more symptoms of PMS is fatigue or cramps. In some embodiments, the PMS is PMDD. In some embodiments, the oxaloacetate or oxaloacetic acid is anhydrous enol-oxaloacetate. In some embodiments, the composition further comprises a pharmaceutical delivery agent. In some embodiments, the pharmaceutical delivery agent is selected amongst the group of capsules, coating agents, encapsulating agents, transdermal patches, dissolving lozenges, suppositories and biphasic delivery systems. In some embodiments, the pharmaceutical delivery agent prevents or reduces exposure of the oxaloacetate to water. In some embodiments, the composition further comprises a pH modifier. In some embodiments, wherein the pH modifier is sodium hydroxide or calcium carbonate. In some embodiments, the composition comprising the oxaloacetate is administered in combination with a pain reliever. In some embodiments, the pain reliever is acetaminophen, ibuprofen, or naproxen. In some embodiments, about 500 mg acetaminophen is administered to the individual. In some embodiments, about 400 mg ibuprofen is administered to the individual. In some embodiments, about 220 mg naproxen sodium is administered to the individual. In some embodiments, the composition comprising the oxaloacetate is administered in combination with an anti-bloating agent. In some embodiments, the anti-bloating agent is pyrilamine maleate or pamabrom. In some embodiments, about 15 mg pyrilamine maleate is administered to the individual. In some embodiments, about 25 mg pamabrom is administered to the individual. In some embodiments, the composition is administered with a pain reliever and with an anti-bloating agent.

In some aspects, the invention provides a method for treating two or more symptoms of premenstrual syndrome (PMS) in an individual, the method comprising administering an effective amount of a composition comprising an oxaloacetate, an oxaloacetic acid, or an oxaloacetate salt to an individual in need thereof; wherein the one or more symptoms of PMS is wherein the one or more symptoms of PMS include one or more of anger, anxiety, depression, or irritability and one or more symptoms of PMS is fatigue or cramps. In some embodiments, the PMS is PMDD. In some embodiments, the oxaloacetate or oxaloacetic acid is anhydrous enol-oxaloacetate. In some embodiments, the composition further comprises a pharmaceutical delivery agent. In some embodiments, the pharmaceutical delivery agent is selected amongst the group of capsules, coating agents, encapsulating agents, transdermal patches, dissolving lozenges, suppositories and biphasic delivery systems. In some embodiments, the pharmaceutical delivery agent prevents or reduces exposure of the oxaloacetate to water. In some embodiments, the composition further comprises a pH modifier. In some embodiments, wherein the pH modifier is sodium hydroxide or calcium carbonate. In some embodiments, the composition comprising the oxaloacetate is administered in combination with a pain reliever. In some embodiments, the pain reliever is acetaminophen, ibuprofen, or naproxen. In some embodiments, about 500 mg acetaminophen is administered to the individual. In some embodiments, about 400 mg ibuprofen is administered to the individual. In some embodiments, about 220 mg naproxen sodium is administered to the individual. In some embodiments, the composition comprising the oxaloacetate is administered in combination with an anti-bloating agent. In some embodiments, the anti-bloating agent is pyrilamine maleate or pamabrom. In some embodiments, about 15 mg pyrilamine maleate is administered to the individual. In some embodiments, about 25 mg pamabrom is administered to the individual. In some embodiments, the composition is administered with a pain reliever and with an anti-bloating agent.

In some embodiments of the above aspects and embodiments, the composition comprises about 100 or about 200, about 300 or about 400 mg oxaloacetate (e.g., anhydrous oxaloacetate). In some embodiments, about 200 mg oxaloacetate is administered to the individual per day. In some embodiments, the composition is administered over a period of about one day, two days, three days, four days or five days. In some embodiments, the composition is administered to the individual about one day, two days, three days, four days or five days prior to menses. In some embodiments, administration of the composition is initiated upon detection of one or more symptoms of PMS. In some embodiments, the composition is administered in combination with a pain reliever. In some embodiments, the pain reliever is acetaminophen, ibuprofen, or naproxen. In some embodiments, about 500 mg acetaminophen is administered to the individual. In some embodiments, about 400 mg ibuprofen is administered to the individual. In some embodiments, about 220 mg naproxen sodium is administered to the individual. In some embodiments, the composition is administered in combination with an anti-bloating agent.

In some aspects, the invention provides a unit dose of oxaloacetate for treating PMS, the unit dose comprising about 10 mg to about 1000 mg oxaloacetate and a pain reliever. In some embodiments, the pain reliever is acetaminophen, ibuprofen, or naproxen. In some embodiments, the unit dose comprises about 500 mg acetaminophen. In some embodiments, the unit dose comprises about 400 mg ibuprofen. In some embodiments, the unit dose comprises about 220 mg naproxen sodium. In some aspects, the invention provides a unit dose of oxaloacetate for treating PMS, the unit dose comprising about 10 mg to about 1000 mg oxaloacetate and an anti-bloating agent. In some embodiments, the anti-bloating agent is pyrilamine maleate or pamabrom. In some embodiments, the unit dose comprises about 15 mg pyrilamine maleate. In some embodiments, the unit dose comprises about 25 mg pamabrom. In some embodiments, the unit dose comprises an oxaloacetate, a pain reliever and an anti-bloating agent. In some embodiments, the unit dose comprises about 100 mg or about 200 mg oxaloacetate. In some embodiments, the unit dose comprises about 200 mg oxaloacetate. In some embodiments, the oxaloacetate or oxaloacetic acid is anhydrous enol-oxaloacetate. In some embodiments, the composition further comprises a pharmaceutical delivery agent. In some embodiments, the pharmaceutical delivery agent is selected amongst the group of capsules, coating agents, encapsulating agents, transdermal patches, dissolving lozenges, suppositories and biphasic delivery systems. In some embodiments, the pharmaceutical delivery agent prevents or reduces exposure of the oxaloacetate to water. In some embodiments, the composition further comprises a pH modifier. In some embodiments, wherein the pH modifier is sodium hydroxide or calcium carbonate. In some embodiments, the PMS is PMDD.

In some aspects, the invention provides an article of manufacture of oxaloacetate for treating PMS, the article of manufacture comprising a composition comprising oxaloacetate and a composition comprising a pain reliever. In some embodiments, the pain reliever is acetaminophen, ibuprofen, or naproxen. In some embodiments, the composition comprises about 500 mg acetaminophen. In some embodiments, the article of manufacture comprises about 400 mg ibuprofen. In some embodiments, the article of manufacture comprises about 220 mg naproxen sodium. In some aspects, the invention provides an article of manufacture of oxaloacetate for treating PMS, the article of manufacture comprising a composition comprising oxaloacetate and a pain reliever. In some aspects, the invention provides an article of manufacture of oxaloacetate for treating PMS, the article of manufacture comprising composition comprising oxaloacetate and a composition comprising an anti-bloating agent. In some aspects, the invention provides an article of manufacture of oxaloacetate for treating PMS, the article of manufacture comprising composition comprising oxaloacetate and an anti-bloating agent. In some embodiments, the anti-bloating agent is pyrilamine maleate or pamabrom. In some embodiments, the article of manufacture comprises about 15 mg pyrilamine maleate. In some embodiments, the article of manufacture comprises about 25 mg pamabrom. In some embodiments, the article of manufacture comprises an oxaloacetate, a pain reliever and an anti-bloating agent. In some embodiments, the article of manufacture comprises about 10 mg to about 1000 mg oxaloacetate. In some embodiments, the composition comprising oxaloacetate comprises about 100 mg or about 200 mg oxaloacetate. In some embodiments, the composition comprising oxaloacetate comprises about 100 mg oxaloacetate. In some embodiments, the oxaloacetate or oxaloacetic acid is anhydrous enol-oxaloacetate. In some embodiments, the composition further comprises a pharmaceutical delivery agent. In some embodiments, the pharmaceutical delivery agent is selected amongst the group of capsules, coating agents, encapsulating agents, transdermal patches, dissolving lozenges, suppositories and biphasic delivery systems. In some embodiments, the pharmaceutical delivery agent prevents or reduces exposure of the oxaloacetate to water. In some embodiments, the composition further comprises a pH modifier. In some embodiments, wherein the pH modifier is sodium hydroxide or calcium carbonate. In some embodiments, the article of manufacture is impervious to moisture. In some embodiments, the article of manufacture further comprises a dessicant. In some embodiments, the PMS is PMDD.

In some aspects, the invention provides a method for treating the combination of suicidal ideation and depression in an individual, the method comprising administering an effective amount of a composition comprising an oxaloacetate, and oxaloacctic acid, or an oxaloacetate salt to an individual in need thereof. In some embodiments, the individual is experiencing symptoms of PMS. In some embodiments, the PMS is PMDD. In some embodiments, said oxaloacetate or oxaloacctic acid is anhydrous enol-oxaloacetate. In some embodiments, the composition further comprises a pharmaceutical delivery agent. In some embodiments, said pharmaceutical delivery agent is selected amongst the group of capsules, coating agents, encapsulating agents, transdermal patches, dissolving lozenges, suppositories and biphasic delivery systems. In some embodiments, the pharmaceutical delivery agent prevents or reduces exposure of the oxaloacetate to water. In some embodiments, the composition further comprises a pH modifier. In some embodiments, the pH modifier is sodium hydroxide or calcium carbonate. In some embodiments, the composition comprises about 100 or about 200, about 300 or about 400 mg oxaloacetate. In some embodiments, about 200 mg oxaloacetate is administered to the individual per day. In some embodiments, the composition is administered over a period of about one day, two days, three days, four days or five days.

BRIEF DESCRIPTION OF THE DRAWINGS

FIG. 1 shows the results of a clinical trial evaluating randomized, double-blinded, placebo controlled cross-over trial for PMS emotional symptoms with oxaloacetate.

DETAILED DESCRIPTION OF THE INVENTION

In accordance with an aspect of the present invention, there is provided a method of treatment of the symptoms of PMS and PMDD by administering an oxaloacetate, an oxaloacetic acid, an anhydrous enol-oxaloacetate or an oxaloacetate salt in a person in need thereof. Also provided is a composition of matter combining said oxaloacetate, oxaloacetic acid, anhydrous enol-oxaloacetate or oxaloacetate salt with either a pain reliever or an anti-bloating agent, or a combination thereof.

The symptoms of PMS and PMDD which include the group of symptoms of muscle ache, bloating, cramping, acne, tender breasts, bloating, fatigue, difficulty concentrating, diminished impulse control, irritability, anxiety, tension, anger, depression, feeling "out of control", insomnia and rapid fluctuations in mood (mood swings). Suicidal thoughts are also sometimes reported. The symptoms typically resolve with the start of menstruation. In some embodiment, the method comprises administration of oxaloacetate, oxaloacetate salts, oxaloacetic acid and/or anhydrous enol-oxaloacetate in the form of a pharmaceutical composition containing one or more pharmaceutically acceptable carriers. For some of the symptoms, a combination of matter is used adding a pain reliever and/or anti-bloating agent.

Oxaloacetate participates in many biochemical reactions in the body, including those in the citric cycle within the mitochondria, gluconeogenesis, urea cycle, glyoxylate cycle, amino acid synthesis, and fatty acid synthesis.

The applicant has seen glutamate reduction in patients via oxaloacetate via three different delivery systems of the anhydrous enol-oxaloacetate; orally in hypromellose capsules, in a lozenge form, and via intravenous injection.

There is an increase in glucose demand in the cerebellum during the late luteal phase which correlates with PMS and PMDD symptoms, dropping blood glucose levels with a compound that promotes lower blood glucose should exacerbate these symptoms. Oxaloacetate has been shown in a clinical trial to lower fasting glucose levels in diabetics (See Yhoshikawa, K, Studies on Anti-diabetic Effect of Sodium Oxaloacetate, *Tohoku J Exp Med*, 1968, 96, 127-141), so art teaches against using oxaloacetate compounds.

Surprisingly, we did see a significant change in PMS and PMDD symptoms with the administration of 100 to 300 mg oxaloacetate, taken either orally or sublingually, even though we were dropping glutamate levels in the brain, and glucose levels in the bloodstream. One skilled in the art would expect symptoms to become more acute, rather than be reduced with decreasing glutamate levels and glucose levels as these low levels are tied to PMS and PMDD symptoms.

In some embodiments, oxaloacetate, oxaloacetate salts, oxaloacetic acid and/or anhydrous enol-oxaloacetate are highly effective in treating the symptoms of acne, tender breasts, fatigue, difficulty concentrating, diminished impulse control, irritability, anxiety, tension, anger, depression, suicidal thoughts, feeling "out of control", insomnia, cramping and rapid fluctuations in mood associated with PMS and PMDD that typically only resolve upon menstruation in these women. With the addition of a pain reliever or anti-bloating agent, the additional symptom of bloating is resolved, and tender breasts and cramping are further relieved.

Recognizing PMS and PMDD in patients is covered in the Diagnostic and Statistical Manual of Mental Disorders, Fifth Edition, and in journal articles such as taught by Liang, Bryan M D, "Recognizing and Treating Premenstrual Dysphoric Disorder", Hospital Physician, August 2003 pp 45-57.

Oxaloacetic Acid, Oxaloacetate and Oxaloacetate Salts

In some embodiments, the present invention provides methods for treating symptoms of PMS and methods for treating symptoms of PMS and PMDD comprising administration of compositions comprising oxaloacetate. Oxaloacetic acid, when dissolved in water, ionizes to oxaloacetate. The oxaloacetate can be in three forms depending on the pH of the solution. At low pH (<1.5) and low temperature (<4° C.) oxaloacetate hydrates. At higher pH, oxaloacetic acid in water occurs in three forms, 1) the hydrated form, 2) a keto form, and 3) an enol form. Outside of water solutions, the solid form of oxaloacetic acid is primarily in the enol form. All forms of oxaloacetic acid and the ion oxaloacetate are absorbed by the body. The hydrated form is mostly converted once it enters the higher pH of the body outside of the intestinal tract to the keto and enol form. As a specific example, at a pH of 6.9, oxaloacetic acid in water is composed of 5% in the hydrated form, 84% in the keto form and 11% in the enol form. Enol-oxaloacetate is converted to keto-oxaloacetate with the enzyme enol-keto tautomerase, a ubiquitous enzyme throughout the human body.

While oxaloacetic acid can be given in any of the three forms and be effective (because the forms change with different pH conditions and enzymatic activity), there is a significant problem with stability that has prevented the commercialization of the compound as a therapeutic agent. (See Cash, U.S. Pat. No. 9,050,306). Keto-oxaloacetic acid decarboxylates spontaneously into pyruvate and carbon dioxide, and neither byproduct of the decomposition is effective in alleviating the symptoms of PMS and PMDD. The stability problems of oxaloacetic acid are well documented in the literature (See U.S. Pat. No. 9,050,306 and references described therein). The lack of stability of oxaloacetic acid has been a source of difficulty in the preparation of a commercial product (Yoshikawa, K, Tohoku J. Exp. Med, (1968) 96:127-141).

The enol and keto form of oxaloacetic acid are tautomers, and in water form a chemical equilibrium. At a pH of 6.9, oxaloacetic acid in water is composed of 5% in the hydrated form, 84% in the keto form and 11% in the enol form. The keto-oxaloacetate decarboxylates quickly to pyruvate. As the keto-oxaloacetate form disappears due to decarboxylation, the enol and hydrated form convert to keto-oxaloacetate, and then also decarboxylate into carbon dioxide and pyruvate, until all the oxaloacetate is consumed. Note that neither of the byproducts of oxaloacetate decarboxylation, carbon dioxide and pyruvate, are effective in treating the symptoms of PMS and PMDD. If there are divalent cations in the fluid, which is very common, the decarboxylation of oxaloacetic acid can happen within a day. Salts of oxaloacetic acid, have been tested and are also not stable, despite the teachings of Yoshikawa. The hydrated form of oxaloacetic acid can be made stable by maintaining it at very low pH, but only for less than one week, at temperatures not exceeding 8° C. However, this does not allow commercial distribution of the product to persons needing treatment for the symptoms of PMS and PMDD with oxaloacetic acid supplementation.

Stabile Oxaloacetic Acid, Oxaloacetate and Oxaloacetate Salts

In some embodiments, the current invention makes use of stable oxaloacetic acid for the treatment of symptoms of PMS and PMDD, which allows for a reasonable shelf life of one year or more. (See Cash, U.S. Pat. No. 9,050,306). In some embodiments, the methods and compositions for the treatment of symptoms of PMS and PMDD use anhydrous enol-oxaloacetic acid which is stable at room temperature for a period exceeding one year. The enol-oxaloacetic acid does not decarboxylate spontaneously and is thus stable if kept dry. Water catalyzes the equilibrium reaction between enol- and keto oxaloacetic acid. Note that only the keto form of oxaloacetic acid decarboxylates into pyruvate and carbon dioxide spontaneously, not the enol-form. There is an energy gap between the enol and keto form which is bridged when the compounds are exposed to water, however, this same energy gap prevents the conversion of the enol to keto form when the product is kept dry. Once there is a conversion to the keto form, decarboxylation can spontaneously occur at temperatures above the freezing point of water. Thus, manufacturing oxaloacetate with a water content of less than 2% and keeping the oxaloacetic acid in a solid state and dry through the use of moisture sealants and/or moisture absorbents creates the commercial shelf-stable enol-oxaloacetate form, even at room temperatures. Drying effectiveness can be increased by increasing the drying time, drying under vacuum, by using anhydrous washes of isopropyl alcohol or ethyl alcohol to absorb the remaining water (and then evaporating the alcohol), or by performing multiple washes with hexane or non-water soluble solvent to physically remove the water, typically after an alcohol wash. The non-water soluble solvent would then be evaporated off. The small amount of non-water soluble solvent wash remaining in the oxaloacetic acid is non-toxic and serves to repel water moisture from entering into the powder to further extend shelf life. Hexane is a residual solvent in many commercial food preparations including decaffeinated coffee, and is not toxic in small quantities. Alternatively, the final wash can be performed with liquefied propane, liquefied butane, ethyl acetate, ethane, carbon dioxide, or nitrous oxide to reduce the water content.

In practice, the isolation of the oxaloacetate from water in the atmosphere for use in the treatment of symptoms of PMS and PMDD can be easily achieved after encapsulation of the oxaloacetic acid by sealing the bottles or placing individual capsules in a plastic blister pack. Reducing the water content below 2% or below 1% along with isolation from the atmosphere, will keep the oxaloacetate in the enol form, and will prevent decarboxylation. Additional measures to prevent decarboxylation include the use of desiccants in the container with the enol-oxaloacetate and the addition of 10% to 90% anhydrous ascorbic acid per weight of oxaloacetic acid, or in some embodiments, 50% anhydrous ascorbic acid per weight of oxaloacetic acid. Ascorbic acid acts as an electron acceptor and reduces the rate of decarboxylation. In some embodiments, the combination of adding anhydrous ascorbic acid, sealing the container, and using an enol-form oxaloacetic acid below a 1% moisture level combine to yield a shelf-life of the product at 30° C. in excess of one year.

In some embodiments, the methods and compositions for the treatment of symptoms of PMS and PMDD comprise a stabilized sodium oxaloacetate (and other salts, solutions and buffered solutions of oxaloacetic acid). Stabilization can be achieved by a biphasic containment system. Sodium oxaloacetate for commercial use can be made by using the solid anhydrous enol-form and combining it with a solution of water plus sodium hydroxide (NaOH) or other basic solution when needed. This can be in the form of a container with two separate compartments, one that contains the basic solution, and one that contains the anhydrous enol-oxaloacetate separated by a breakable barrier. When sodium oxaloacetate (or other salt) is needed, the barrier between the basic solution and the anhydrous oxaloacetate is broken, and oxaloacetate salt is quickly formed in solution. The solubility of oxaloacetic acid in water is 100 mg/ml, allowing rapid digestion of the anhydrous enol-oxaloacetic acid. In some embodiments, a biphasic containment system includes a flexible capsule, such as a gel cap which can be compressed by hand or with teeth to break an inner seal between the sodium hydroxide solution and the solid anhydrate enol-oxaloacetate. In other embodiments, the biphasic containment system includes an intravenous (IV) bag with two compartments, one with an IV fluid and the other with anhydrous enol-oxaloacetic acid separated by a breakable barrier. When needed, the breakable barrier is ruptured, and the two components are mixed. The IV fluid can be a buffered solution, a non-buffered solution, an acidic solution, a basic solution or a neutral solution. In yet another embodiment, the biphasic containment system has two separate containers; one for the solid oxaloacetic acid, and one for the liquids. Two separate containers will allow the solid oxaloacetic acid to be placed in storage below 0° C., while the liquid container is kept at a different temperature. Storing the dry oxaloacetic acid at −20° C. enables the use of commonly available commercial oxaloacetic acid, without the additional drying step of the preparation. Again when needed, the two containers are joined and mixed to yield the oxaloacetate salt solution.

Pharmaceutical Compositions and Methods of Administration

Oxaloacetate can be administered to an individual at therapeutically effective doses for the treatment of symptoms of PMS and PMDD. In some embodiments, oxaloacetate is administered to an individual for the treatment of suicide ideation and depression.

As used herein, "oxaloacetate" includes oxaloacetic acid, the salt of the acid, or oxaloacetate in a buffered solution as well as mixtures thereof. In some embodiments of the current invention, the oxaloacetic acid can be in the form of anhydrous enol-oxaloacetic acid.

Effective Dose

A therapeutically effective dose refers to that amount of oxaloacetate sufficient to result in the desired effect such as the amelioration of symptoms relating to PMS and PMDD. In some embodiments, the dose is from about 100 mg oxaloacetate to about 1,000 mg oxaloacetate. In some embodiments, the dose is from about 100 mg oxaloacetate to about 300 mg oxaloacetate. In some embodiments, the does is less than or equal to any of about 100 mg, 200 mg, 300 mg, 400 mg, 500 mg, 600 mg, 700 mg, 800 mg, 900 mg, or 1000 mg. The oxaloacetate can be in the form of oxaloacetate, oxaloacetic acid, oxaloacetate salt or anhydrous enol-oxaloacetate.

Toxicity and therapeutic efficacy of oxaloacetate for use in the treatment of PMS or PMDD can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population or PMS or PMDD patients). The dose ratio between toxic and therapeutic effects is the therapeutic index and it can be expressed as the ratio $LD_{50}/ED_{50}$. The $LD_{50}$ of oxaloacetate is above 5 g/kg of body weight. The "no observable adverse effects level" (NOAEL) in a 90-day sub-chronic rat study was 500 mg/kg (the highest dose in the test). Oxaloacetate has a very low toxicity, as would be expected from a chemical involved in the Citric Acid Cycle of every cell.

In some embodiments of the invention, an effective dose of oxaloacetate administered by a lozenge is from about 0.2 mg to about 50 mg of oxaloacetate for the treatment of symptoms of PMS and/or PMDD for each kg of body weight. In some embodiments, the effective dose of oxaloacetate is between about 1 mg and about 4 mg for each kg of body weight. Due to the acidity of the compound, the effective dose must be pH balanced. In some embodiments, effective oral dosing ranges from about 0.2 mg to about 50 mg of oxaloacetate for each kg of body weight. In some embodiments, the effective dosage range between about 1 mg to about 4 mg of oxaloacetate for each kg of body weight. For example, an adult female weighing approximately 70 kg would be administered between about 70 mg to about 280 mg of oxaloacetate orally per day. Dermally, topical formulations comprising concentrations of about 0.2 to 16 mM of oxaloacetate are effective but again need to be pH balanced and in a transdermal system that is extremely low in water content (to prevent degradation of the oxaloacetate).

Formulations

Pharmaceutical compositions for use in accordance with the present invention may be formulated in conventional manner using one or more physiologically acceptable carriers or excipients. Thus, oxaloacetate and its physiologically acceptable salts and solvates may be formulated for administration by inhalation or insufflation (either through the mouth or the nose) or oral, buccal, topical, transdermal, parenteral, or rectal administration. In the case of inhalation, the administration of oxaloacetate will provide aging benefits directly to lung tissue, even if the dosage of oxaloacetate administered is less than is needed to benefit the entire organism.

Oxaloacetate is acidic with a pH in water about 2.3. The acidity is unlikely to affect organisms that ingest the compound in beneficial amounts as the interior conditions of the stomach are also very acidic (around 1.0). The acidity may affect other tissues, including but not limited to the skin or lungs, that may allow delivery of the direct application of oxaloacetate. Therefore, in another embodiment, a composition of matter can be created by mixing oxaloacetate with a buffer solution or a base or used as a salt of oxaloacetate so the delivered compound is not caustic. This will enable higher concentrations of oxaloacetate to be delivered safely to the organism, especially if the oxaloacetate is not delivered by oral ingestion.

For oral administration for the treatment of symptoms of PMS and/or PMDD, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets may be coated by methods well known in the art. Liquid preparations for oral administration may take the form of, for example, non-water solutions, syrups or suspensions, or they may be presented as a dry product for constitution with water or other suitable vehicle immediately before use (due to decarboxylation concerns). Water acts as a catalyst which allows for the conversion of solid enol-oxaloacetate to convert to the liquid keto-oxaloacetate form which spontaneously decarboxylates into pyruvate and carbon dioxide. Such non-water liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

A topical application through a trans-dermal patch or cream is yet another embodiment for administration of oxaloacetate for treating the symptoms of PMS and PMDD. The topical pharmaceutical compositions of the present invention may be made into a wide variety of product types. These include, but are not limited to lotions, creams, beach oils, gels, sticks, sprays, ointments, pastes, and mousses. These product types may comprise several types of pharmaceutical carrier systems including, but not limited to solutions, emulsions, gels and solids. The topical pharmaceutical compositions of the present invention formulated as solutions typically include a pharmaceutically-acceptable organic solvent. The terms "pharmaceutically-acceptable organic solvent" refer to a solvent which is capable of having dissolved therein the oxaloacetate, and possesses acceptable safety properties (e.g., irritation and sensitization characteristics). Examples of a suitable pharmaceutically acceptable organic solvent include, for example, monohydric alcohols, such as ethanol, and polyhydric alcohols, such as glycols. If the topical pharmaceutical compositions of the present disclosure are formulated as an aerosol and applied to the skin as a spray-on, a propellant is added to a solution composition.

In some embodiments, the oxaloacetate for use in treating symptoms of PMS and/or PMDD may be formulated from a solution carrier system is a cream or ointment. In some embodiments, the cream or ointment is a non-water based cream or ointment. An ointment can comprise a simple base of animal or vegetable oils or semi-solid hydrocarbons (oleaginous). An ointment can include from about 0.1% to about 2% of a thickening agent. Examples of suitable thickening agents include: cellulose derivatives (e.g., methyl cellulose and hydroxy propylmethylcellulose), synthetic high molecular weight polymers (e.g., carboxyvinyl polymer and polyvinyl alcohol), plant hydrocolloids (e.g., karaya gum and tragacanth gum), clay thickeners (e.g., colloidal magnesium aluminum silicate and bentonite), and carboxyvinyl polymers (CARBOPOLS'; sold by B. F. Goodrich Company, such polymers are described in detail in Brown, U.S. Pat. No. 2,798,053, issued Jul. 2, 1975). A more complete disclosure of thickening agents useful herein can be found in Sagarin, Cosmetics, Science and Technology, 2nd Edition, Vol. 1, pp. 72-73 (1972). If the carrier is formulated as an emulsion, from about 1% to about 10%, for instance, from about 2% to about 5%, of the carrier system comprises an emulsifier. Suitable emulsifiers include non-ionic, anionic or cationic emulsifiers. Exemplary emulsifiers are disclosed in, for example, McCutcheon's Detergents and Emulsifiers, North American Edition, pages 317-324 (1986). In some embodiments, emulsifiers are anionic or nonionic, although other types can also be employed.

An emulsion carrier system useful in the topical pharmaceutical compositions for the treatment of symptoms of PMS and/or PMSS is a microemulsion carrier system. Such a system comprises from about 9% to about 15% squalane; from about 25% to about 40% silicone oil; from about 8% to about 20% of a fatty alcohol; from about 15% to about 30% of polyoxyethylene sorbitan mono-fatty acid (commercially available under the trade name Tweens) or other nonionics; and from about 7% to about 20% water. This carrier system is combined with the therapeutic agents described above, with the oxaloacetate carried in the non-water portion.

The topical pharmaceutical compositions for the treatment of symptoms of PMS and/or PMDD can also include a safe and effective amount of a penetration enhancing agent. Other conventional skin care product additives may also be included in the compositions of the present invention. For example, collagen, elastin, hydrolysates, primrose oil, jojoba oil, epidermal growth factor, soybean saponins, mucopolysaccharides, and mixtures thereof may be used. Various vitamins can also be included in the compositions of the present invention. For example, Vitamin A, and derivatives thereof, Vitamin B2, biotin, pantothenic, Vitamin D, and mixtures thereof can be used.

In yet a further embodiment of the current invention, the oxaloacetate delivered topically can be mixed with a penetration enhancing agent such as dimethylsulfoxide (DMSO), combinations of sucrose fatty acid esters with a sulfoxide or phosphoric oxide, or eugenol, that allows faster migration of the oxaloacetate into the dermal tissues and then further into deeper cellular tissues.

In some embodiments, the disclosed compounds are administered through a topical delivery system for the treatment of symptoms of PMS and PMDD. Implantable or injectable polymer matrices, and transdermal formulations, from which active ingredients are slowly released are also well known and can be used in the disclosed methods. The controlled release components described above can be used as the means to deliver the disclosed compounds. The compositions can further include components adapted to improve the stability or effectiveness of the applied formulation, such as preservatives, antioxidants, skin penetration enhancers and sustained release materials. Examples of such components are described in the following reference works hereby incorporated by reference: Martindale—The Extra Pharmacopoeia (Pharmaceutical Press, London 1993) and Martin (ed.), Remington's Pharmaceutical Sciences.

Controlled release preparations can be achieved by the use of polymers to complex or absorb oxaloacetate. The controlled delivery can be exercised by selecting appropriate macromolecule such as polyesters, polyamino acids, polyvinylpyrrolidone, ethylenevinyl acetate, methylcellulose, carboxymethylcellulose, and protamine sulfate, and the concentration of these macromolecule as well as the methods of incorporation are selected in order to control release of active compound.

In another embodiment, transdermal patches, steady state reservoirs sandwiched between an impervious backing and a membrane face, and transdermal formulations, can also be used to deliver oxaloacetate for the treatment of symptoms of PMS and/or PMDD. Transdermal administration systems are well known in the art. Occlusive transdermal patches for the administration of an active agent to the skin or mucosa are described in U.S. Pat. Nos. 4,573,996, 4,597,961 and 4,839,174, which are hereby incorporated by reference. One type of transdermal patch is a polymer matrix in which the active agent is dissolved in a polymer matrix through which the active ingredient diffuses to the skin. Such transdermal patches are disclosed in U.S. Pat. Nos. 4,839,174, 4,908,213 and 4,943,435, which are hereby incorporated by reference. In one embodiment, the steady state reservoir carries doses of oxaloacetate in doses from about 2 mg to 40 mg per day.

Present transdermal patch systems are designed to deliver smaller doses over longer periods of time, up to days and weeks. A rate-controlling outer microporous membrane, or micropockets of the disclosed oxaloacetate dispersed throughout a silicone polymer matrix, can be used to control the release rate. Such rate-controlling means are described in U.S. Pat. No. 5,676,969, which is hereby incorporated by reference. In another embodiment, the oxaloacetate is released from the patch into the skin of the patient in about 20-30 minutes or less.

These transdermal patches and formulations can be used with or without use of a penetration enhancer such as dimethylsulfoxide (DMSO), combinations of sucrose fatty acid esters with a sulfoxide or phosphoric oxide, or eugenol. The use of electrolytic transdermal patches is also within the scope of the methods disclosed herein. Electrolytic transdermal patches are described in U.S. Pat. Nos. 5,474,527, 5,336,168, and 5,328,454, the entire contents of which are hereby incorporated by reference.

Oxaloacetate may be formulated for parenteral administration for the treatment of symptoms of PMS and/or PMDD by injection, e.g., by bolus injection or continuous infusion. The injected oxaloacetate can be mixed with other beneficial agents prior to injection including but not limited to antibiotics and other medications, saline solutions, blood plasma, and other fluids. Immediate contact of elevated levels of oxaloacetate with the vascular system cells will result in the reduction in age-related diseases such as hardening of the arteries, even if the amounts of oxaloacetate are insufficient to provide age-related benefits to the entire organism. Formulations for injection may be presented in unit dosage form, e.g., in ampoules or in multi-dose containers, with an added preservative. The compositions may take such forms as suspensions, solutions or emulsions in oily or non-aqueous vehicles, and may contain formulatory agents such as suspending, stabilizing and/or dispersing agents. Alternatively, the active ingredient may be in powder form for constitution with a suitable vehicle, e.g., sterile pyrogen-free water, before immediate use.

Oxaloacetate may also be formulated in rectal compositions such as suppositories or retention enemas, e.g., containing conventional suppository bases such as cocoa butter or other glycerides.

In addition to the formulations described previously, oxaloacetate may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions for the treatment of symptoms of PMS and/or PMDD may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

In another embodiment of the current invention, oxaloacetate can be combined with a pain reliever to decrease cramping pain, headache pain, or muscle pain occurring in PMS and PMDD. Said pain relievers can include ibuprofen, acetaminophen, aspirin, indomethacin, oxyphenbutazone and naproxen. Examples of pain relievers used in formulations for PMS and PMDD and their dosage can be found in U.S. Pat. No. 5,155,105 by Jones et al. and other pain relievers used in formulations are known in the art.

In some embodiments, the pain reliever is acetaminophen, ibuprofen, or naproxen. In some embodiments, about 100 mg to about 1000 mg acetaminophen is administered to the individual in combination with oxaloacetate treatment. In some embodiments, about any of 100 mg, 200 mg, 300 mg, 400 mg, 500 mg, 600 mg, 700 mg, 800 mg, 900 mg, or 1000 mg acetaminophen is administered to the individual in combination with oxaloacetate treatment. In some embodiments, about 500 mg acetaminophen is administered to the individual in combination with oxaloacetate treatment. In some embodiments, about 100 mg to about 1000 mg ibuprofen is administered to the individual in combination with oxaloacetate treatment. In some embodiments, about any of 100 mg, 200 mg, 300 mg, 400 mg, 500 mg, 600 mg, 700 mg, 800 mg, 900 mg, or 1000 mg ibuprofen is administered to the individual in combination with oxaloacetate treatment. In some embodiments, about 400 mg ibuprofen is administered to the individual in combination with oxaloacetate treatment. In some embodiments, about 100 mg to about 500 mg naproxen (e.g., naproxen sodium) is administered to the individual in combination with oxaloacetate treatment. In some embodiments, about any of 100 mg, 140 mg, 180 mg, 220 mg, 260 mg, or 300 mg naproxen is administered to the individual in combination with oxaloacetate treatment. In some embodiments, about 220 mg acetaminophen is administered to the individual in combination with oxaloacetate treatment.

In yet another embodiment of the current invention, oxaloacetate can be combined with a diuretic or anti-bloating compound to reduce periodic water retention or buildup in the body. Such diuretics can include both pharmacological and/or nutritional herbal compounds. Said diuretics can include potassium compounds (such as potassium citrate) pamabrom, pyrilamine maleate, caffeine, and hydrochlorothiazide. Typically potassium compounds are limited to deliver no more than 100 mg of potassium per dose. The dosage and uses of other diuretics can be found in U.S. Pat. No. 5,155,105 by Jones et al. Herbal nutritionals can also have a diuretic effect. These would include but not be limited to dandelion root and leaf, juniper berry, cranberry powder (fruit), hibiscus extract (flower), chamomile (flower), grape seed powder, parsley, red raspberry powder (leaf), goldenrod, *Uva Ursi* extract (leaf), *Agathosma Betulina* (leaf), *Fucus Vesiculosus*, Mango Seed powder, and paprika. Other nutritional and pharmacological diuretics are known in the art.

In some embodiments, the anti-bloating agent is pyrilamine maleate or pamabrom (1:1 mixture of 2-amino-2-methyl-1-propanol and 8-bromotheophyllinate). In some embodiments, about 5 mg to about 25 mg pyrilamine maleate is administered to the individual in combination with oxaloacetate treatment. In some embodiments, about any of 5 mg, 10 mg, 15 mg, 20 mg, or 25 mg pyrilamine maleate is administered to the individual in combination with oxaloacetate treatment. In some embodiments, about 15 mg pyrilamine maleate is administered to the individual in combination with oxaloacetate treatment. In some embodiments, about 10 mg to about 50 mg pamabrom is administered to the individual in combination with oxaloacetate treatment. In some embodiments, about any of 10 mg, 15 mg, 20 mg, 25 mg, 30 mg, 35 mg, 40 mg, 45 mg or 500 mg pamabrom is administered to the individual in combination with oxaloacetate treatment. In some embodiments, about 25 mg pamabrom is administered to the individual in combination with oxaloacetate treatment.

In some embodiments, the oxaloacetate is administered to the individual in combination with a pain reliever and an anti-bloating agent. For example, one or more of acetaminophen, ibuprofen, or naproxen and one or more of pyrilamine maleate or pamabrom.

While others in the art have combined pain relievers with diuretics (such as U.S. Pat. No. 5,155,105), to deal with some of the symptoms of PMS and PMDD, including bloating, and head, muscle and cramping pain, these combinations have had no effect on mood swings, depression, anxiety, fatigue and anger, which are affected by oxaloacetate supplementation in the current invention. Combination of oxaloacetate with pain relievers and diuretics provide a more effective overall solution to the problems of PMS and PMDD because it also address the emotional side of PMS and PMDD.

As used herein, "treatment" is an approach for obtaining beneficial or desired clinical results. For purposes of this invention, beneficial or desired clinical results include, but are not limited to, alleviation of symptoms of PMS and PMDD, diminishment of symptoms of PMS and PMDD, and stabilized (e.g., not worsening) symptoms of PMS and PMDD.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise. It is understood that aspects and variations of the invention described herein include "consisting" and/or "consisting essentially of" aspects and variations.

While the present invention has been particularly shown and described with reference to exemplary embodiments thereof, it will be understood by those of ordinary skill in the art that various changes in form and details may be made therein without departing from the spirit and scope of the present invention as defined by the following claims.

EXAMPLES

Below are some case studies and a human trial, both of which show significant improvement in symptoms. While acne can be measured by inspection, the other symptoms rely upon the internal feelings of the patient. To measure symptoms that deal with tender breasts, fatigue, difficulty concentrating, diminished impulse control, irritability, anxiety, tension, anger, depression, suicidal thoughts, feeling "out of control", insomnia, cramping and rapid fluctuations in mood, one skilled in the art must rely on the interpretation of patient. This can be done through an interview with an expert, such as a medical doctor, or through validated survey forms that specifically address these symptoms. Examples of these forms that have been validated by independent clinical trial include:
  Buss Perry Aggression Questionnaire (Anger)
  Clinical Anger Scale (Anger)
  Cohen-Perceived-Stress Scale (Anxiety)
  Generalized-Anxiety-Scale (Anxiety)
  Generalized Anxiety Disorder 7-item (GAD-7) scale (Anxiety)
  Beck's Depression Inventory (Depression)
  Center for Epidemiologic Studies Depression Scale (Depression)
  Hospital Anxiety and Depression Scale (Anxiety and Depression)
  Premenstrual Assessment Form (anger, depression, fatigue and anxiety)
  Mood Calendar Tracking (anger, depression, fatigue and anxiety)

Example 1

In a clinical trial, 30 women with PMS were first evaluated for PMS and then presented with the nutritional supplement "benaGene" (100 mg anhydrous enol-oxaloacetate with a pharmaceutically acceptable excipient of 150 mg anhydrous ascorbic acid). Only one patient did not report a substantial improvement, indicative of a positive response rate of 97%. Typically, in 30-60 minutes from taking 1 to 2 capsules, once per day, many or all PMS symptoms would either resolve fully or would be reduced significantly. The patients would only take the supplement during days they experienced PMS symptoms, and not the rest of the month. 3 capsules did not produce a superior response to 2 capsules.

Example 2

A 28 year-old woman experienced severe anger and depression one day a month, right before her period, every month. She took two capsules of 100 mg anhydrous enol-oxaloacetate on that day. She reported that while the anger and depression were not completely resolved, they were reduced in intensity to the point where she could manage the symptoms easily.

Example 3

A woman diagnosed with PMDD had a history of extreme cramping (pain level 10), suicidal thoughts, and difficulty with anger and anxiety. The cramping was not relieved by Midol or Aspirin. The woman was despondent even after her symptoms of PMDD left because of guilt over her behavior during this time period. She took 200 mg oxaloacetate in a hypromellose capsule carrier, and experienced immediate relief from all symptoms. She reported that it was like a 1,000 pound weight being taken off her shoulders.

Example 4

The woman in Example 3 continued to take oxaloacetate each month for the next three months and monitored her progress. She took one pill starting about 10 days before her period, and continued taking 1 pill daily until the first sign of PMS, when she increased the dosage to 2 capsules per day until the 2nd day of her period. The symptoms of PMDD completely resolved. She reported that "I am no longer a suicidal, psychotic crazy person every month. And I know it is the supplements because this will be the 3rd month with no PMDD and that is NOT a coincidence."

Example 5

A woman presented with severe PMDD ever since she was 13 years old. She is now 26. Typically, the patient had to take-off from work 3 days out of each month, and self-seclude, because she could not be with people. She started taking 2 capsules benaGene (each 100 mg anhydrous enol-oxaloacetate with acceptable pharmacological carriers). All symptoms resolved and she no longer has to take off from work. The improvements with anhydrous enol-oxaloacetate have continued for over 2 years with this patient.

Example 6

A 25-year old woman presented with severe anxiety attacks and fatigue during the week before menstruation. At the start of these panic attacks or during extreme fatigue, she placed two lozenges of 100 mg anhydrous enol-oxaloacetate with a suitable pH adjustment and pharmaceutical carrier under her tongue for 5 minutes. The panic attack subsided in less than 5 minutes and fatigue was greatly reduced.

Example 7

A randomized, double blinded placebo-controlled cross-over trial was conducted using 200 mg oxaloacetate per day as the active ingredient, and rice flour as the placebo ingredient. An Institutional Review Board (IRB) has approved the clinical plan, and patients have signed the human consent forms.

Patients were located from across the United States. Consent forms and survey questionnaires were filled out on-line. The patients and the lead investigator were unaware of which product, Active or Placebo, the patients were receiving.

Inclusion Criteria for the trial:
Able to give informed consent and follow instructions per the protocol
Female with history of mood swings, anxiety or depressed mood associated with PMS
Ages 21 to 50 at the start of the study
Not pregnant
Exclusion Criteria for the trial:
A formal diagnosis of Major Depression
Previously taken Oxaloacetate as a supplement
Participation in other drug studies or use of other investigational products within 30 days prior to baseline
If unwilling to discontinue use of other nutritional supplements taken for the purpose of PMS modulation during the study
Any unstable or clinically significant condition that would impair the subject's ability to comply with study follow up.
No diagnosis of Premenstrual Dysphoric Disorder (PMDD) (a severe form of PMS).

After signing the human consent forms, the patient took four different surveys to assess their current emotional state during PMS.

The Beck Depression Inventory modified to examine the week prior to the woman's period (21 questions)
The Cohen Perceived Stress form, modified to examine the week prior to the woman's period (10 questions).
The Generalized Anxiety Disorder 7-Item Scale modified to examine the week prior to the woman's period (7 questions).
The Buss Perry Aggression questionnaire modified to examine the week prior to the woman's period (29 questions).

The time to fill out the composite 4-survey questionnaire is less than 30 minutes.

The questionnaires are filled out on-line and made available to investigator team. The women in the study did not have access to the questionnaires they previously completed.

After a "baseline" 4-survey questionnaire was completed by the women, they would be randomly sent either the Active oxaloacetate compound (200 mg oxaloacetate) or the Placebo (200 mg rice flour). The women would take a daily dose of the compound received, starting with their menstrual period, and continuing daily until the following menstrual period. At that following menstrual period, the women would again complete the 4-survey questionnaire.

At this point in the clinical trial, the women would have received the second shipment of whatever product they did not test previously-Rice flour capsules for those that initially received oxaloacetate, and oxaloacetate capsules for those that received rice flour capsules. This is a "cross-over" type design. The women take the new product staring on a menstrual period, and continue taking it daily until a following menstrual period. The then again complete the 4-survey questionnaire.

In this trial, each woman completed a baseline survey, and a survey after approximately 28 days for oxaloacetate, and a survey after approximately 28 days for rice flour. 26 women completed the study. Half of the women took oxaloacetate first, and the other half took a placebo first.

Table 1 shows the results of this trial. FIG. 1 shows the results graphically. P values were calculated using a student's T test, using a two-tailed distribution with paring of the data to the individual.

TABLE 1

Clinical results of a randomized, double-blinded, placebo controlled cross-over trial for PMS emotional symptoms with oxaloacetate.

| | Reduction from baseline | | Reduction from baseline | | Reduction from Placebo | |
|---|---|---|---|---|---|---|
| | Oxaloacetate | P Value | Placebo | P Value | Oxaloacetate | P Value |
| Beck's Depression Inventory | 50.88% | 1.5E−06 | 34.01% | 0.0034 | 25.57% | 0.11 |
| Cohen Perceived Stress | 34.35% | 2.9E−08 | 20.46% | 0.0054 | 16.51% | 0.096 |
| Generalized Anxiety Disorder | 49.73% | 1.9E−07 | 30.11% | 0.0018 | 28.08% | 0.042 |
| Buss-Perry Aggression Scale | 15.10% | 0.00016 | 6.49% | 0.11 | 9.22% | 0.1 |

As can be seen by the results, oxaloacetate supplementation at 200 mg per day was highly statistically significant in reducing the PMS symptoms of depressed mood, perceived stress, anxiety and aggression (anger). The oxaloacetate results were consistently improved over placebo, as were the p values showing significance.

Based on review of this data, and on submitted animal and cellular work, the US FDA concurred with the following structure/function claim allowed to be placed on the oxaloacetate product bottle:

"Oxaloacetate may help alleviate the mild to moderate psychological and/or behavioral symptoms associated with Premenstrual Syndrome (PMS)."

Example 8

The clinical trial of Example 7 was repeated with 19 women, except that the trial was single blinded. The placebo was sent to all women first, and the oxaloacetate active second. The trial was modified in this manner because in the previous trial, it was calculated that oxaloacetate supplementation had a beneficial effect beyond the time of ingestion. This should not have come as a complete surprise to us, as oxaloacetate exerts a beneficial effect on gene expression (movement towards the calorie restriction metabolic state) that can have positive effects for several weeks after discontinuation of the product. To better measure the oxaloacetate effect, therefore, oxaloacetate was given second in this trial.

The results of this trial mirror the results of the first trial, again indicating that oxaloacetate successfully reduces the emotional symptoms of PMS.

TABLE 2

Clinical results of a single-blinded, placebo controlled cross-over trial for PMS emotional symptoms with oxaloacetate.

|  | Reduction from baseline | | Reduction from baseline | | Reduction from Placebo | |
| --- | --- | --- | --- | --- | --- | --- |
|  | Oxaloacetate | P Value | Placebo | P Value | Oxaloacetate | P Value |
| Beck's Depression Inventory | 54.42% | 0.0000002 | 27.51% | 0.0006 | 37.12% | 0.012 |
| Cohen Perceived Stress | 36.67% | 0.0000004 | 16.20% | 0.0013 | 24.40% | 0.00009 |
| Generalized Anxiety Disorder | 54.23% | 0.0000021 | 26.15% | 0.015 | 38.02% | 0.008 |
| Buss-Perry Aggression Scale | 17.81% | 0.0022 | 4.36% | 0.18 | 14.06% | 0.017 |

P values were calculated using a student's T test, using a two-tailed distribution with paring of the data to the individual.

Example 9

In the clinical trials within Examples 7 and 8, the Beck's Depression Inventory was used. One portion of the Beck's Depression Inventory specifically deals with "Suicidal Ideation" (thoughts about committing suicide). The survey scores the relative severity of suicidal ideation via numerical scoring as follows:

Score Value
0 I don't have any thoughts of killing myself.
1 I have thoughts of killing myself, but I would not carry them out.
2 I would like to kill myself
3 I would kill myself if 1 had the chance.

The results of Clinical Trial 1 and 2 were compiled to examine the Suicidal Ideation of the women who participated in this clinical trial. Out of the 45 women in both trials, 31 women experienced a score above 0 in the baseline survey. No women in the completed study who scored 0 in the baseline study increased their suicidal ideation score. In order to examine suicidal ideation statistically, women with a 0 score on their baseline survey were removed from the analysis. P values were calculated using a student's T test, using a two-tailed distribution with paring of the data to the individual.

TABLE 3

Oxaloacetate reduces Suicidal Ideation over initial baseline measurements

| Reduction from Baseline | | | |
| --- | --- | --- | --- |
| Oxaloacetate | P Value | Placebo | P Value |
| 47.90% | 0.000038 | 35.40% | 0.0025 |

As can be seen, oxaloacetate is highly significant in reducing suicidal ideation over baseline values. The improvement is better than placebo in both scoring and in p value. Of particular interest in this small study was that with oxaloacetate two of the three women that initially stated that "I would kill myself if I had the chance" (3 points) moved their answer to "I don't have any thoughts of killing myself" (0 points). The other one woman that initially scored a 3 was reduced to a 1 point with oxaloacetate, reduced to "I have thoughts of killing myself, but I would not carry them out.

Reduction in suicidal ideation may save the lives of these women. It is unexpected and novel that oxaloacetate both reduced depressed mood, and also reduced suicidal ideation, as typically medications that lower depression increase suicidal ideation.

What is claimed is:

1. A method for treating Premenstrual Dysphoric Disorder (PMDD) in an individual, the method comprising administering an effective amount of a composition comprising an oxaloacetate, an oxaloacetic acid, or an oxaloacetate salt in the individual in need thereof.

2. A method for treating one or more symptoms of PMDD in an individual, the method comprising administering an effective amount of a composition comprising an oxaloacetate, an oxaloacetic acid, or an oxaloacetate salt to an individual in need thereof; wherein the one or more symptoms of PMS include one or more of acne, tender breasts, bloating, fatigue, difficulty concentrating, diminished impulse control, irritability, anxiety, tension, anger, depression, suicidal thoughts, insomnia, or cramping.

3. The method of claim 2, wherein the method is for treating two or more symptoms of PMS in an individual, wherein the two or more symptoms of PMS include two or more of acne, tender breasts, bloating, fatigue, difficulty concentrating, diminished impulse control, irritability, anxiety, tension, anger, depression, suicidal thoughts, insomnia, or cramping.

4. The method of claim 3, wherein the method is for treating three or more symptoms of PMS in an individual, wherein the three or more symptoms of PMS include three or more of acne, tender breasts, bloating, fatigue, difficulty concentrating, diminished impulse control, irritability, anxiety, tension, anger, depression, suicidal thoughts, insomnia, or cramping.

5. The method of claim 2, wherein the symptoms of PMS include acne, bloating, fatigue, irritability, anxiety, anger, depression, insomnia or cramping.

6. The method of claim 2, wherein the one or more symptoms of PMS further comprises mood swings.

7. The method of claim 6, wherein said oxaloacetate or oxaloacetic acid is anhydrous enol-oxaloacetate.

8. The method of claim 1, wherein the composition further comprises a pharmaceutical delivery agent.

9. The method of claim 8 wherein said pharmaceutical delivery agent is selected amongst the group of capsules, coating agents, encapsulating agents, transdermal patches, dissolving lozenges, suppositories and biphasic delivery systems.

10. The method of claim 8, wherein the pharmaceutical delivery agent prevents or reduces exposure of the oxaloacetate to water.

11. The method of claim 1, wherein the composition further comprises a pH modifier.

12. The method of claim 11, wherein the pH modifier is calcium carbonate.

13. The method of claim 1, wherein the composition comprises about 100 or about 200, about 300 or about 400 mg oxaloacetate.

14. The method of claim 1, wherein about 200 mg oxaloacetate is administered to the individual per day.

15. The method of claim 1, wherein the composition is administered over a period of about one day, two days, three days, four days or five days.

16. The method of claim 1, wherein the composition is administered to the individual about one day, two days, three days, four days or five days prior to menses.

17. The method of claim 1, wherein administration of the composition is initiated upon detection of one or more symptoms of PMS.

18. The method of claim 1, wherein the composition is administered in combination with a pain reliever.

19. The method of claim 18, wherein the pain reliever is acetaminophen, ibuprofen, or naproxen.

20. The method of claim 18, wherein about 500 mg acetaminophen, about 400 mg ibuprofen, or about 220 mg naproxen sodium is administered to the individual.

21. The method of claim 1, wherein the composition is administered in combination with an anti-bloating agent.

22. The method of claim 21, wherein the anti-bloating agent is pyrilamine maleate or pamabrom.

23. The method of claim 21, wherein about 15 mg pyrilamine maleate or about 25 mg pamabrom is administered to the individual.

* * * * *